United States Patent [19]
Eggers

[11] Patent Number: 5,807,392
[45] Date of Patent: Sep. 15, 1998

[54] RESISTIVELY HEATED CUTTING AND COAGULATING SURGICAL INSTRUMENT

[76] Inventor: Philip E. Eggers, 5366 Reserve Dr., Dublin, Ohio 43017

[21] Appl. No.: 816,300

[22] Filed: Mar. 13, 1997

Related U.S. Application Data

[62] Division of Ser. No. 398,007, Mar. 2, 1995, Pat. No. 5,611,798.
[51] Int. Cl.⁶ ..................................................... A61B 17/39
[52] U.S. Cl. .............................. 606/31; 606/29; 219/230; 219/233; 219/235; 219/241
[58] Field of Search .................................. 606/28, 29, 31; 219/230, 233, 235–239, 241

[56] References Cited

U.S. PATENT DOCUMENTS

| | | | |
|---|---|---|---|
| 5,445,635 | 8/1995 | Denen et al. | 606/31 |
| 5,593,406 | 1/1997 | Eggers et al. | 606/29 |

*Primary Examiner*—Lee S. Cohen
*Attorney, Agent, or Firm*—Mueller and Smith, LPA

[57] ABSTRACT

A surgical instrument having a resistively-heated heating component responsive to a power source for generating thermal excitation effective for cutting tissue and carrying out hemostasis. The surgical instrument includes a support assembly having two leg extensions connected in heat transfer relationship with the heating component. Two thermal transition regions are provided within the heating component and have extents effective to provide a decreasing temperature gradient and to restrict temperature levels exhibited at the support assembly. The support assembly is formed of high thermally conductive material and extends from the transition regions to an elongate shaft. This shaft is in heat transfer relationship with the support assembly and is formed from a high thermally conductive material. Together, the shaft and support assembly act as a heat buffer such that temperature levels exhibited at the support assembly are restricted to levels atraumatic to tissue while the heating component is heated to temperatures effective for cutting and hemostasis. A hand engagable handle connects to the shaft. The surgical instrument may be powered from existing, conventional electrosurgical generators having bipolar outputs, and, in this regard, additionally includes circuit components selected for effecting power transfer impedance matching between the electrosurgical generator and the heating component.

3 Claims, 6 Drawing Sheets

FIG. 11

RESISTIVELY HEATED CUTTING AND COAGULATING SURGICAL INSTRUMENT

This application is a division, of application Ser. No. 08/398,007, filed Mar. 2, 1995, now U.S. Pat. No. 5,611,788.

BACKGROUND

During typical surgical procedures, patient bleeding is controlled not only to avoid excess blood loss, but also for such purposes as assuring that the vision of the performing surgeon is not obstructed or the operation otherwise disrupted. In "open" surgery, bleeding traditionally has been controlled through the use of ties, clamps, blotting, or the like. Further, commencing in the 1920's, a technology emerged referred to as "electrosurgery" in which tissue is cut and blood coagulated with a select application of electrical current. The latter effect is referred to as hemostasis.

Today, electrosurgery is one of the more widely used hemostatic surgical modalities for cutting tissue and carrying out coagulation. Electrosurgical instrumentation falls into one of two categories, monopolar devices and bipolar devices. Generally, surgeons are trained in the use of both monopolar and bipolar electrosurgical techniques, and essentially all operating rooms will be found equipped with the somewhat ubiquitous instrumentality for performing electrosurgery, the electrosurgical generator.

A somewhat pioneer monopolar electrosurgical device was developed by William T. Bovie. This early device described, for example, in U.S. Pat. No. 1,813,902, issued on Jul. 14, 1931 entitled "Electrosurgical Apparatus" has met with acceptance over the years within the surgical community to the extent that current versions are referred to as the "Bovie." Current such devices typically consist of a handle having a first or "active" electrode extending from one end. The other end of the handle is electrically coupled to an electrosurgical generator which provides a high frequency electric current in either an A.C. cutting mode or a pulsed coagulating mode. A remote control switch is attached to the generator and commonly extends to a foot switch located in proximity to the operating theater. During an operation, a second or "return" electrode, having a much larger surface area than the active electrode, will be positioned in contact with the skin of the patient. To remove tissue, the surgeon brings the active electrode in close proximity with the tissue and activates the foot controlled switch. Electrical current then arcs from the distal portion of the active electrode and flows through tissue to the larger return electrode. In a cutting mode, electrical arcing and corresponding current flow results in a highly intense but localized heating which causes cell destruction and tissue severance. Generally, the device is then switched to a pulsed, higher voltage input to perform in a coagulating mode.

For the bipoloar modality, no return electrode attached to the patient is used. Instead, a second electrode is closely positioned adjacent to the first electrode, with both electrodes being attached to a handle. As with monopolar devices, this handle is electrically coupled to an electrosurgical generator. When this generator is switch activated, electrical current arcs from the end of the first electrode to that of the second electrode. In turn, tissue disposed between the electrodes is cut and blood coagulated. In practice, several electrodes may be employed, and depending on the relative size or locality of the electrodes, one or more electrodes may be active.

Both the monopolar and bipolar devices have inherent shortcomings. For example, since monopolar devices use relatively large radio frequency (RF) currents, the patient may be subject to unwanted risks of RF burns occurring inadvertently at locations where the patient is grounded. Additionally, the path of current flow through tissue often presents the risk of tissue necrosis (i.e., tissue and organ cell death) along errant current flow paths. Equally, tissue necrosis may occur at excessive depths located at the point of application near the active electrode. In any event, a considerable portion of the RF current necessarily is dissipated through the patient, a condition of risk.

By contrast, the bipolar modality overcomes some of the more undesirable characteristics of monopolar devices in that excessive necrosis is reduced, and current is not passed extensively through the body. Since current arcs between adjacent electrodes, blood vessels are readily cauterized. Bipolar devices, however, generally exhibit poor cutting ability. Additionally, it is difficult to accurately locate the arc between the two electrodes with respect to tissue under resection.

Perhaps, as a consequence of the inherent disadvantages associated with monopolar and bipolar modalities, investigators have considered resistively-heated surgical blades or cutting implements to provide a capability for simultaneously cutting tissue and coagulating blood. In their early form, these instruments consisted of a surgical wire or blade which was electrically connected to a power supply. As current passed through the device, the blade was resistively heated to a high temperature. Thereafter, the surgical wire or blade was used to incise tissue but with the added advantage that the generated and localized heat served to cauterize at the incision.

One problem associated with these early thermally based surgical devices is that the wire or blade will rapidly cool upon contact with tissue. As the blade cools, it becomes less and less effective for providing hemostasis. Additionally, as the blade cools below a temperature threshold, tissue tends to stick to it, resulting in obstruction of the cutting edge. If additional power is supplied to accommodate for the cooling effect, overheating may occur in some regions of the blade. Such overheating may be accompanied by unwanted tissue burning or blade destruction. Steel blades exhibit these problems in particular (especially where heating is a function of $I^2R$ and resistance increases with temperature).

One solution to these problematic heating phenomena has been to provide a surgical blade which has a cutting edge or tissue engaging region with a self-regulating temperature characteristic. Self-regulation (also known as autoregulation) involves maintaining the cutting edge of the surgical blade within an elevated, preselected temperature range. An approach for attaining self-regulation has been to employ a ferromagnetic material in constructing the end or heating element of the surgical instrument. When AC current, or more particularly RF current, is passed through such ferromagnetic material, the current density tends to concentrate near its outer surface. This current density attenuates exponentially as distance into the material from the surface increases, a phenomenum known as the "skin effect."

The depth of the skin effect (i.e., the distance of penetrating current density into the ferromagnetic material) is defined as the depth at which current is reduced to approximately 37% of its surface value. This depth may be represented mathematically as follows:

$$\text{skin depth} = (5 \times 10^3)\sqrt{\rho/\mu f}$$

where skin depth is measured in centimeters, $\rho$ is electrical resistivity in ohmcentimeters, $\mu$ is electrical relative magnetic permeability for the ferromagnetic material, and $f$ is frequency of the applied alternating electric potential.

In ferromagnetic materials (such as iron, nickel, cobalt, and respective alloys), adjacent atoms and molecules couple their magnetic moments together in rigid parallelism (an interaction known as exchange coupling) in spite of the randomizing tendency of the thermal motion of atoms. If the temperature of such material is raised above a "Curie" temperature, specific for each ferromagnetic material, the noted exchange coupling suddenly disappears. As a result, these materials exhibit large changes in relative permeability as the temperature of the ferromagnetic material transitions through the Curie temperature. As seen from the above-mathematical equation, since the relative permeability is known to change in response to the temperature of the material, the associated skin depth also will change. This relationship between skin depth and temperature enables ferromagnetic material based instruments to achieve auto-regulation.

The heating elements of surgical devices can be constructed from ferromagnetic material which is selected to have a Curie temperature at or near the auto-regulation temperature desired for a particular surgical application. As RF current passes through the ferromagnetic material, the heating element will resistively heat to approximately the Curie temperature. Once the cutting edge contacts tissue, both it and the area surrounding it will cool to a level below the Curie temperature. In response to this Curie transition, skin depth will decrease which, in turn, results in an increased resistance of the cooled region (the resistance being a function of the ferromagnetic material's resistivity multiplied by length and divided by area). A corresponding increase in power supply will accompany this increase in resistance. The temperature then will tend to again increase due to resistive heating toward the Curie temperature. Thus, auto-regulation of the surgical blade or wire around the Curie temperature is achieved.

By way of example, the heating element of a surgical device may be formed from an iron-nickel alloy having a Curie temperature of about 450° C. While the heating element is above the Curie temperature, the relative permeability (shown in the above equation) remains near one. However, when the cutting portion of the heating element contacts tissue, the temperature will correspondingly drop and the relative permeability will rise, for example, to 100 or even 1000. The associated skin depth, in turn, decreases by more than 10 to 1. Correspondingly, an increase in power is supplied to the heating element, which increases resistive heating—thus achieving auto-regulation.

A disadvantage associated with resistively heated devices, including those which employ ferromagnetic heating elements, is concerned with a lack of sufficient localization of heat at the actual cutting edge. In this regard, the entire heating element including the support for its cutting edge is heated toward a Curie temperature suited for cutting. This poses a risk that the support portion of the heating element may contact tissue or organs not selected for incision. Additionally, since a larger portion of the heating component is heated, the time period required for the cutting region to cool down to safe levels posing no threat of burning can be quite significant. This time period, for example, may be five seconds or more, an interval generally considered unacceptable for surgical procedures. Further, during a laparoscopic or endoscopic procedure, the view of the surgeon is confined to a camera-generated two dimensional image at a monitor, such as a TV screen. The heated element, however, may be moved out of the camera's limited field of view during the several seconds which are required for cool-down, thereby endangering tissue that may come in contact therewith.

Another disadvantage associated with resistively heated devices is concerned with a perceived requirement that they must be powered by a specially designed power supply, typically incorporating a constant current source. Such electrical drive systems generally are configured to be unique to the properties of a particular heating element and are not of a universal nature, such that they would be usable with different resistively heated tools. For example, some devices require not only a constant current source but a complex control which senses a voltage decrease as the cutting edge approaches Curie temperature. Thereafter, the control system turns the current source off for a predetermined time to reduce the temperature of the cutting edge. Of course, such added equipment requirements pose budgetary concerns to health care institutions.

Essentially all hospitals, health care centers, clinics, and the like which have facilities for performing surgical procedures are equipped with an ample number of conventional electrosurgical generators. These generators are designed to operate in monopolar and bipolar modes to, in turn, drive conventional instruments. In this regard, the generators commonly have two output sets which accommodate monopolar devices and bipolar devices. The generators, however, are not compatible with resistively heated surgical devices.

It therefore would be desirable to provide a resistively-heated surgical instrument where only a confined region of the heating element reaches the elevated temperatures required for cutting and coagulation of tissue and where the heating element rapidly cools to temperatures atraumatic to tissue and organs. Any connective member attached to the heating element for providing support thereto should remain at temperatures below a threshold which would otherwise produce unwanted thermal damage to surrounding tissue.

It also would be desirable to provide a low-cost resistively-heated surgical instrument which can be operated using conventional electrosurgical generators already in wide use in operating facilities.

In addition to the above, it further would be desirable to provide a resistively-heated surgical instrument that overcomes patient risks heretofore associated with monopolar electrosurgical devices and which improves the cutting ability heretofore associated with bipolar electrosurgical devices.

It also would be desirable to offer a resistively-heated surgical instrument with replaceable working tips to allow the surgeon to select a specific working end configuration and size particularly suited to the tissue cutting and coagulating requirements at a given stage of a surgical procedure.

It also would be desirable to provide a resistively-heated surgical instrument which has the ability to precisely control the location and amount of thermal energy delivered to tissue.

SUMMARY

The present invention is addressed to surgical instruments of a variety having a resistively-heated cutting component. The surgical instrument is structured to substantially minimize opportunities for unwanted or accidental thermal damage to tissue during surgery. In this regard, two thermal transition regions are provided within the heating component which is formed in a continuous loop-like configuration. Adjacently disposed to these transition regions is a tissue engaging region which resistively heats to temperatures effective for cutting and carrying out coagulation when RF current supplied from a separate electrosurgical generator is passed therethrough. While the tissue engaging region is elevated to these cutting and coagulating temperatures, temperatures witnessed at the thermal transition regions are substantially lower. In this regard, the thermal transition regions provide a decreasing temperature gradient away from the tissue engaging region. Thus, the total area elevated to temperatures effective to cut tissue with accompanied hemostasis is confined generally to the tissue engaging region. A surgeon utilizing the surgical instrument of the present invention has the capability to improve cutting precision and reduce the risk to the patient of inadvertent thermal damage to tissue.

As another advantage, since the tissue engaging region of the heating component is confined to a discrete area, the time period required for this region to cool to temperature levels atraumatic to tissue is significantly reduced. In this regard, a support assembly is connected to and in heat transfer relationship with the heating component. This support assembly is formed from a high thermally conductive and low electrically resistive material which, in turn, acts as a large heat sink for the heating component. While the tissue engaging region is elevated to cutting and hemostatic temperature levels (generally above 300° C.), the support assembly is maintained at temperature levels atraumatic to adjacent tissue and organs (generally below 60° to 70° C.). Heat conduction is directed from the heating component (formed of low thermally conductive material) to the support assembly (formed of high thermally conductive material). This heat conduction effects rapid cool-down of the tissue engaging region after RF current is discontinued to the heating component and additionally aids to restrict elevated temperature levels to locations adjacent the first and second thermal transition regions.

Additionally, the support assembly preferably has a cross-sectional area several times larger than the surface area of the tissue engaging region. This larger cross-sectional area further expedites heat conduction from the cutting region and increases heat dissipation from the support assembly to ambient air.

As another aspect, the surgical instrument incorporates a shaft which is connected to the support assembly for providing support thereto. This shaft has an outer surface or housing formed of high thermally conductive material which is in heat transfer communication with the support assembly. The outer surface thus acts as a large heat sink or buffer and aids in restricting the support assembly to lower temperature levels atraumatic to tissue and organs while the tissue engaging region is elevated to higher cutting and coagulating temperatures. Additionally, the outer surface increases the overall heat sink region with respect to the heating component and thus further aids to effect rapid cool down of the heating component.

Another advantage of the invention provides for the powering of the surgical instrument from existing conventional electrosurgical generators having bipolar outputs. In this regard, circuit components, provided with the surgical instrument, are selected for effecting power transfer impedance matching between the electrosurgical generator and the heating component.

As an additionally advantage, the surgical instrument has a replaceable working end assembly which allows the performing surgeon to select a specific working tip configuration and size particularly suited to the tissue cutting and coagulating requirements at a given stage of the surgical procedure. These replaceable tips may include longer shafts for use in endoscopic or laparoscopic procedures or shorter shafts for use in open procedures.

As another advantage, the present invention is provided as a low-cost hemostatic surgical instrument effective for precisely cutting and coagulating tissue.

The invention, accordingly, comprises the apparatus and system possessing the construction, combination of elements, and arrangement of parts which are exemplified in the following detailed disclosure.

For a fuller understanding of the nature and objects of the invention, reference should be made to the following detailed description taken in connection with the accompanying drawings.

DETAILED DESCRIPTION OF THE INVENTION

The open procedure and endoscopic or laparoscopic procedure instruments of the invention necessarily have similarity in geometry of length and diameter as well as in functional implementation by the surgeon with devices in the market place. However, the design of these instruments, while constrained by a need to emulate the shape of those surgical instruments, varies in a manner achieving very precise cutting and coagulation of tissue without requiring the flow of electrical current through the patient's tissue. This precise cutting and coagulation of tissue is achieved using existing electrosurgical generators. With the present invention, these conventional electrosurgical generators can be adapted to become a power source for totally different surgical instruments and techniques wherein current flow is confined to a resistively heated element which is integrally combined with a cutting and coagulation working end of the instrument. Of importance, thermal cutting is achieved with a unique localization and isolation of the heated element, thus avoiding unwanted thermal damage to adjacent tissue.

Figure 1:
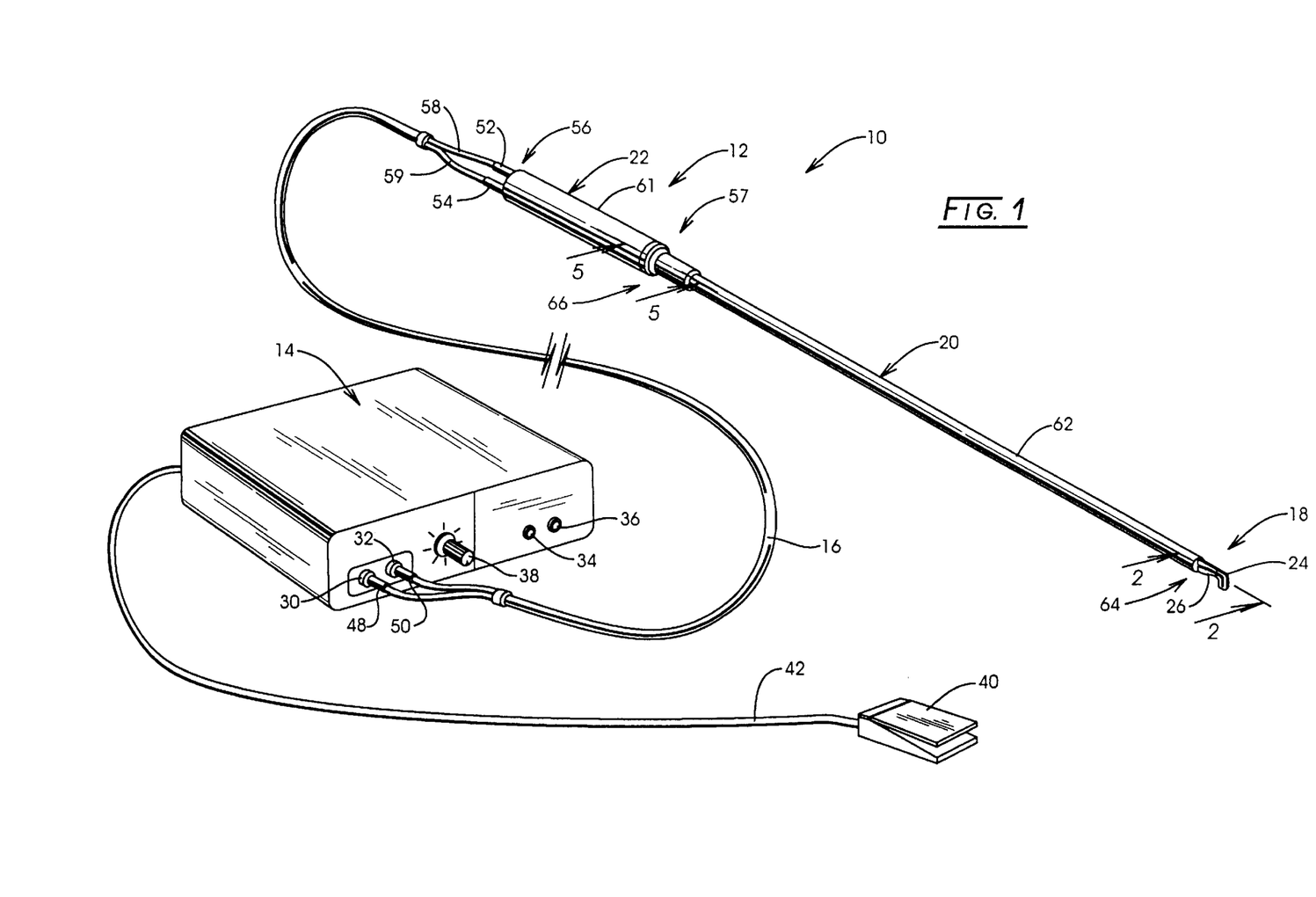
FIG. 1 is a perspective view of a surgical instrument according to the invention electrically coupled via a cable to a power source.

Referring to FIG. 1, an illustrative embodiment of a system for carrying out the thermal cutting of tissue with hemostasis is shown generally at 10. This system 10 includes a surgical instrument 12, a power source 14, and an elongate cable 16. Cable 16 is connectable in electrical power transfer relationship between those components.

Instrument 12 is shown configured for laparoscopic surgical applications and includes a working end assembly 18 which is supported by an elongate accessing tube-like support assembly formed as a shaft 20. Shaft 20 is dimensioned for selectable insertion through the port of a cannula and its rearward or proximal end is supported by an instrument handling portion or handle 22 which is grasped by a surgeon for maneuvering a resistive working tip or heating component 24. Heating component 24 serves to provide thermal cutting with hemostasis and, for the present embodiment, is seen to extend normally from a support assembly 26.

Power source 14 may be a conventional electrosurgical generator of the type having bipolar output terminals 30 and 32 and monopolar output terminals 34 and 36. Such devices, for example, are marketed by Conmed/Aspen of Utica, N.Y.; Berchtold of Tuttlingen, Germany, Birtcher of Irvine, Calif., Erbe or Tübingen, Germany, Martin of Tuttlingen, Germany, and Valleylab of Boulder, Colo. Various levels of bipolar output power from generator 14 may be selected by adjusting a control knob 38. Additionally, power to surgical instrument 12 may be actuated to "on" or "off" conditions using a foot pedal control 40 connected to generator 14 by foot pedal cable 42. Alternatively, hand actuated controls (not shown) such as a switch, for example, may be provided at handle 22. One end of cable 16 includes two cable input connectors 48 and 50 which are removably connectable with respective bipolar output terminals 30 and 32. Handle 22 includes an instrument input 56 at one end and a separate, oppositely disposed instrument output 57. The opposite end of cable 16 includes two cable output connectors 52 and 54 which are removably connectable to the rearward instrument input 56. In order to provide a complete current flow path for electrical communication between electrosurgical generator 14 and surgical instrument 12, cable 16 consists of two separate electrically conducting leads 58 and 59.

For the laparoscopic embodiment shown, assembly or shaft 20 is cylindrically configured having an outer tube surface 62 and oppositely disposed ends 64 and 66. The length of shaft 20 may be selected according to the intended surgical use at hand. For example, in "open" surgical procedures, shaft 20 may be provided having lengths as short as several centimeters or as long as 15 to 20 centimeters. For endoscopic or laparoscopic surgical procedures, shaft 20 typically may be in the range from 30 to 45 centimeters in length. Additionally, shaft 20 may be flexible as, for example, required for esophageal and intestinal endoscopy procedures.

Handle 22 preferably is configured having a casing 61 which is hand graspable and easily manipulable during a surgical procedure. FIG. 1 shows handle 22 to be cylindrically shaped. During a surgical procedure, foot pedal 40 typically is placed on the floor for access by the surgeon. When foot pedal 40 is foot actuated, generator 14 provides radio frequency (RF) alternating current through output terminals 30 and 32, along cable 16, and to instrument input 56. That current then confronts load related components at handle 22 and is conducted through shaft 20 to support assembly 26 and heating component 24. As a consequence, the temperature of heating component 24 rises due to joulean heating to a temperature effective for carrying out thermal cutting of tissue with accompanied hemostasis for so long as generator 14 retains an "on" condition.

Figure 2:
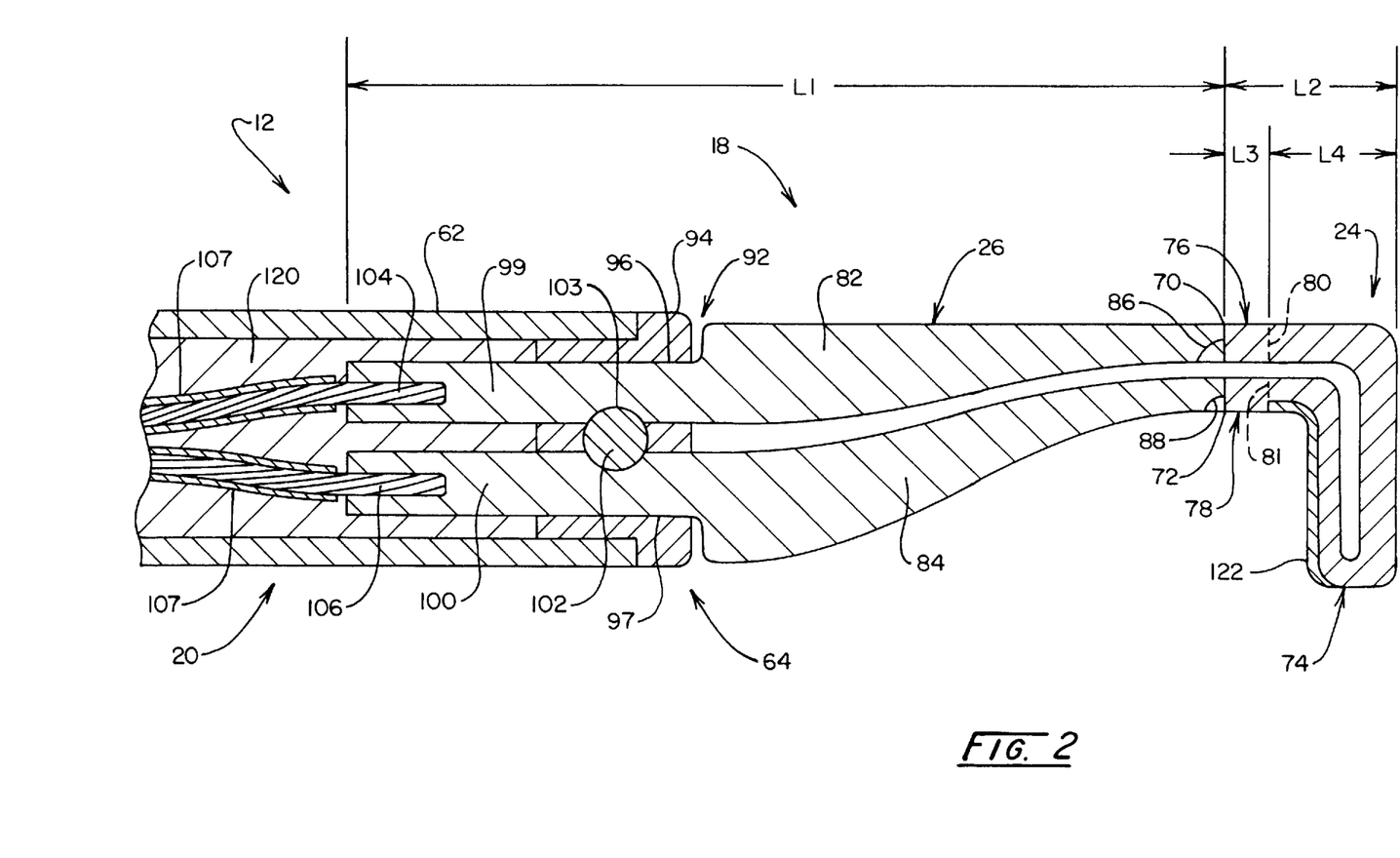
FIG. 2 is a cross sectional view of the surgical instrument of FIG. 1 taken along the plane 2—2 shown therein.

Turning to FIG. 2, the construction of working end assembly 18 attached to end 64 of assembly 20 is shown in greater detail. Heating component 24 is configured somewhat as a continuous loop extending from two adjacent termini 70 and 72. A tissue engaging region 74 of the loop-shaped component 24 serves to engage and thermally cut tissue, a cutting approach simultaneously providing hemostasis. A rearwardly positioned wedge shaped or sharper cutting edge 122 is seen formed within a portion of region 74. As part of the structuring achieving proper temperatures for cutting and coagulating at the working tip or heating component 24, while also achieving heat localization and rapid cool down upon removing power, thermal transition regions shown respectively at 76 and 78 extend inwardly from termini 70 and 72 to respective borders 80 and 81 shown as dashed lines.

Heating component 24 is disposed in adjacency with and supported by support assembly 26. Assembly 26 is configured having two legs 82 and 84 which are connected in electrical and heat transfer communication with termini 70 and 72 of heating component 24. Such connection is provided at interface defining respective leg ends 86 and 88. The interface between ends 86 and 88 of support assembly 26 and thermal transition regions 76 and 78 may be formed by electron beam welding, laser welding, or edge (roll) bonding. For example, a continuous strip of selected materials for assembly 26 and heating component 24 first can be manufactured and thereafter joined together. The desired configuration (i.e., shape and size) can be obtained by blanking (i.e., die-cutting), electrodischarge machining, laser cutting, or other processes. Working end assembly 18 also may be coated with a thin layer (for example 0.1 to 10 microns) of oxidation resistant, biocompatible material such as titanium, platinum, or the like.

Legs 82 and 84 extend rearwardly to form a bifurcate connector portion 92 which is configured for connection with shaft 20. An electrically insulating end cap assembly 94 is affixed to end 64 of shaft 20 and is formed having two openings 96 and 97 configured for receiving and supporting connector extensions 99 and 100 of respective legs 82 and 84. Connector extensions 99 and 100 may be secured within respective openings 96 and 97 with a locking pin 102. In this regard, cap assembly 94 is configured to have a cross hole into which pin 102 is received. Each connector extension 99 and 100 additionally may be recessed or notched at 103 to lockably receive a portion of pin 102 for a more secure attachment.

As shown in FIG. 1, electrical communication is provided from generator 14 to support assembly 26 and heating component 24. FIG. 2 shows that two leads 104 and 106, electrically coupled with leads 58 and 59, respectively, of cable 16 (FIG. 1), extend within shaft 20 and electrically connect to connector extensions 99 and 100. This electrical connection may be accomplished in a variety of ways, such as soldering, welding, mechanical crimping, or the like. Leads 104 and 106 preferably are formed from heavier gauge copper wire (such as 12 to 16 gauge) and are covered with an insulation 107. Additionally, a thermally conductive, electrically insulating potting material 120 may be provided within end 64 of shaft 20 to electrically insulate leads 104 and 106 from outer surface 62 and to secure these leads and extensions 99 and 100 within shaft 20. Such material also will provide thermal communication betwen support 26 and tube 20 to further reduce temperature rise in the former. Examples of suitable potting material include ceramic and polymeric materials such as epoxy or silicon (such as DP-270 manufactured by 3M Company of St. Paul, Minn.).

In the present embodiment, heating component 24 is formed from a ferromagnetic material and, as such, is able to achieve auto or self-regulation of temperature. In this regard, still looking to FIGS. 1 and 2, when pedal 40 is actuated and RF current is supplied to working end assembly 18, heating component 24 commences to heat up due to joulean heating. This current resistively heats that portion of component 24 extending beyond borders 80 and 81 toward its effective Curie temperature (effective Curie temperature for a ferromagnetic material typically is 50° to 100° Celsius below the actual published Curie temperature of the material). During a surgical application, heating component 24 will exhibit an increased resistance when brought in contact with tissue disposed at a relatively cooler temperature. This decrease in temperature confines the flow of RF current generally to the surface or "skin" layer of heating component 24 with the attendant increase in resistance. As heating component 24 moves out of the tissue and into contact with air, such heat transfer is significantly decreased, resulting in a temperature increase. When this temperature again approaches the effective Curie temperature, permeability decreases and the skin depth (the area through which the current is mostly confined) increases, thereby resulting in lower resistance levels and correspondingly lowered heating. Correspondingly, the power drawn from generator 14 declines, and the noted regulation around the effective Curie temperature is achieved. In order to effect thermal cutting accompanied with hemostasis, heating component 24 typically operates at temperatures between about 300° C. and 750° C.

Depending upon the surgical application, the ferromagnetic material with which heating component 24 is formed may be selected to achieve a specific auto-regulation temperature. For example, heating component 24 may be formed from an iron/chromium alloy containing about 13% chromium in which the significant change in permeability occurs over the range from about 500° to 700° C. (such as martensitic stainless steal 420 manufactured by Joslyn Stainless Steal Company of Ft. Wayne, Ind.) or formed from an iron/nickel alloy containing about 42% nickel in which significant change in permeability occurs over the range from about 400° to 480° C. (such as Alloy 49 manufactured by Carpenter Technology Corporation of Reading, Pa.). An iron/nickel alloy is advantageous in that it has a relatively low thermal conductivity yet a high magnetic permeability below its Curie temperature. Accordingly, at the operating frequency of commercially available electrosurgical generators, the majority of the current flowing in heating component 24 will be confined to within about 0.03 to 0.09 millimeters of the outer surface. In a preferred embodiment, the operating temperature range for heating component 24 corresponding to the range of cooling loads for contact with tissue (maximum cooling load) and for contact with air (minimum cooling load) may be selected in the range of about 350° C. to 750° C.

An important feature of instruments formed according to the present invention is concerned with localizing heat originating at heating component 24 and effecting rapid cool-down of this heating component when power is discontinued. This localization of heat serves to avoid unwanted damage to adjacent tissue and organs and to minimize the overall area elevated to higher temperatures. Such localization promotes rapid cool down upon removal of power. To this end, support assembly 26 is formed from a material having a high thermal conductivity and low electrical resistivity. Examples of such material include copper, silver, aluminum, molybdenum, or alloys based on one or more of these metals. The configuration of and material used in assembly 26 should be selected to minimize joulean heating as RF current passes therethrough and to maximize heat conduction from heating component 24. Thus, as heating component 24 heats toward its effective Curie temperature, heat is transferred by thermal conduction to assembly 26. In this regard, while tissue engaging region 74 of component 24 is at an elevated temperature (for instance above 350° C.) it may be used to effect cutting of tissue with accompanied hemostasis. Heat generated in tissue engaging region 74 is conducted across borders 80 and 81 and is dissipated along thermal transition regions 76 and 78. Thereafter, this heat is further conducted to and dissipated along support assembly 26 and in particular from termini 70 and 72 along thermally and electrically conductive legs 82 and 84. During heat conduction, thermal transition regions 76 and 78 serve as thermal chokes to localize heat to region 74 as it extends from borders 80 and 81 within that tissue engaging region. Accordingly, transition regions 76 and 78 act as a short temperature buffer region which provides a region of decreasing temperature(i.e., temperature gradient) from borders 80 and 81 to respective termini 70 and 72. Thus, temperature levels exhibited at borders 80 and 81 are greater than those at termini 70 and 72. Proper selection of ferromagnetic material and design configurations (such as dimensional restraints and shape) of working end assembly 18 further reduces temperature levels exhibited at regions 76 and 78 and legs 82 and 84. These temperatures are restricted to levels atraumatic to tissue (below about 50° to 70° C.) even when the temperature of tissue engaging region 74 is elevated toward effective Curie temperature (above 300° C.).

In order to further aid in rapid cool down of heating component 24 and maintain support assembly 26 at reduced temperature levels (below 60° to 70° C. while tissue engaging region 74 is at temperature levels of 300° C. and greater), heat conduction also is provided between support tube or assembly 20 and assembly 26. As noted, joulean heat originating in tissue engaging region 74 is conducted across transition regions 76 and 78 and along legs 82 and 84 to connector extensions 99 and 100. Thereafter, this heat is further conducted to assembly or tube 20 through its thermally conductive potting material 120. Tube 20 preferably is formed from a high thermally conducting material such as copper, aluminum, a copper alloy, or an aluminum alloy (for example, a copper alloy containing about 98% copper). The support assembly 20 structure, in effect, provides a heat sink of sufficient area and volume for dissipating heat to ambient air by radiation and/or convection modes of heat transfer.

As shown in FIG. 2, support assembly 26 extends from leg ends 86 and 88 a distance to oppositely disposed connector extensions 99 and 100, respectively. The ratio of this total distance, labeled as L1, to the cross sectional area A of support assembly 26 when combined with thermal conductivity K may be expressed as a thermal resistance R. Equation 1 below shows this relationship:

$$R = L1/(KA) \qquad \text{(Equation 1)}$$

The thermal resistance R of support assembly 26 over length L1 can be estimated by dividing the length of each leg 82 and 84 into a finite number of subregions (n) each having length $L_i$, average cross-section area $A_i$, and thermal conductivity $K_i$. The sum of the thermal resistances for all of these sub-regions then equals the total thermal resistance for the entire assembly 26. Equation 2 below shows this relationship:

$$R = \sum_{i=1}^{n} L_i/(K_i A_i) \qquad \text{(Equation 2)}$$

Each leg 82 and 84 of assembly 26 preferably has a thermal resistance, R, not greater than about 100° C./watt and more preferably not greater than 50° C./watt. Correspondingly, assembly 26 preferably has a thermal conductivity, C, of at least about 0.6 watt/cm°C. The thermal resistance of thermal transition regions 76 and 78 (as defined by Equation 1) additionally should not be less than about 200° Celsius\watt. Equations 1 and 2 illustrate that the thermal resistance, R, value is a function of length and cross sectional area. Thus, thermal resistance may be varied to suit the needs of the designer by changing the length or cross sectional area of legs 82 and 84. Similarly, the length and cross-sectional area of heating component 24 may be varied to achieve different thermal resistance values.

High thermal resistance can be realized through a combination of design parameters, such as selecting heating component 24 to have a low thermal conductivity. Additionally, the cross-section area of thermal transition regions 76 and 78 should be small compared to their lengths, shown as L3. A practical upper limit on L3 is concerned with the need to maintain the total heated area of working end assembly 18 as small as possible in order to minimize the possibility of unwanted thermal necrosis of tissue near the site of tissue targeted for cutting and hemostasis. The lower limit on the cross-sectional area of thermal transition regions 76 and 78 further is constrained by a requirement for structural integrity of working end assembly 18 for use in manipulating tissue as well as cutting tissue. Additionally, the distance L3, representing the length of the transition regions 76 and 78, should be sufficient so that tissue engaging region 74 is maintained at temperatures effective to hemostatically cut tissue while at the same time support assembly 26 is maintained at much lower temperatures atraumatic to tissue. The lengthwise extent of these regions preferably is about 0.1 inch (2.5 millimeters). A dimension L4 represents the longitudinal axial extent of tissue engaging region 74, while the dimension L2 represents the combined length of distances L3 and L4.

The overall dimensions of the exemplary configuration shown in FIG. 2 are summarized as follows:

```
L1 = 25 millimeters
L2 = 5 millimeters
L3 = 2.5 millimeters
L4 = 2.5 millimeters
T1 = 0.75 millimeters
T2 = 0.25 millimeters
D1 = 5.0 millimeters
```

Where, T1 is the thickness of heating component 24 and support assembly 26; T2 is the thickness of outer surface 62; and D1 is the diameter of outer surface 62.

Heating component 24, being in the noted loop-like configuration serves to locate the tissue engaging region 74 behind target tissue. Cutting action then is achieved, for example by pulling surgical instrument 12 toward the target tissue. The tissue, in turn, is severed and, simultaneously, hemostasis is provided. Tissue engaging region 74 may be manufactured with a sharpened cutting edge 122 which can cut when at elevated temperatures, i.e., 300° C. or greater. Selection of material for heating component 24 advantageously is based on design considerations other than the requirement to have a cutting grade material suited for a mechanically sharp edge (i.e., an edge that will cut tissue at room temperature). Additionally, heating component 24, and in particular tissue engaging region 74, may be coated with an electrically insulating coating which reduces the accumulation of tissue, coagulum, or like material. Such coatings may include silicone, fluorocarbon polymers, or other suitable materials known to those skilled in the art, and suitable for operation up to the maximum temperature of the particular ferromagnetic metal or alloy selected.

Figure 3:
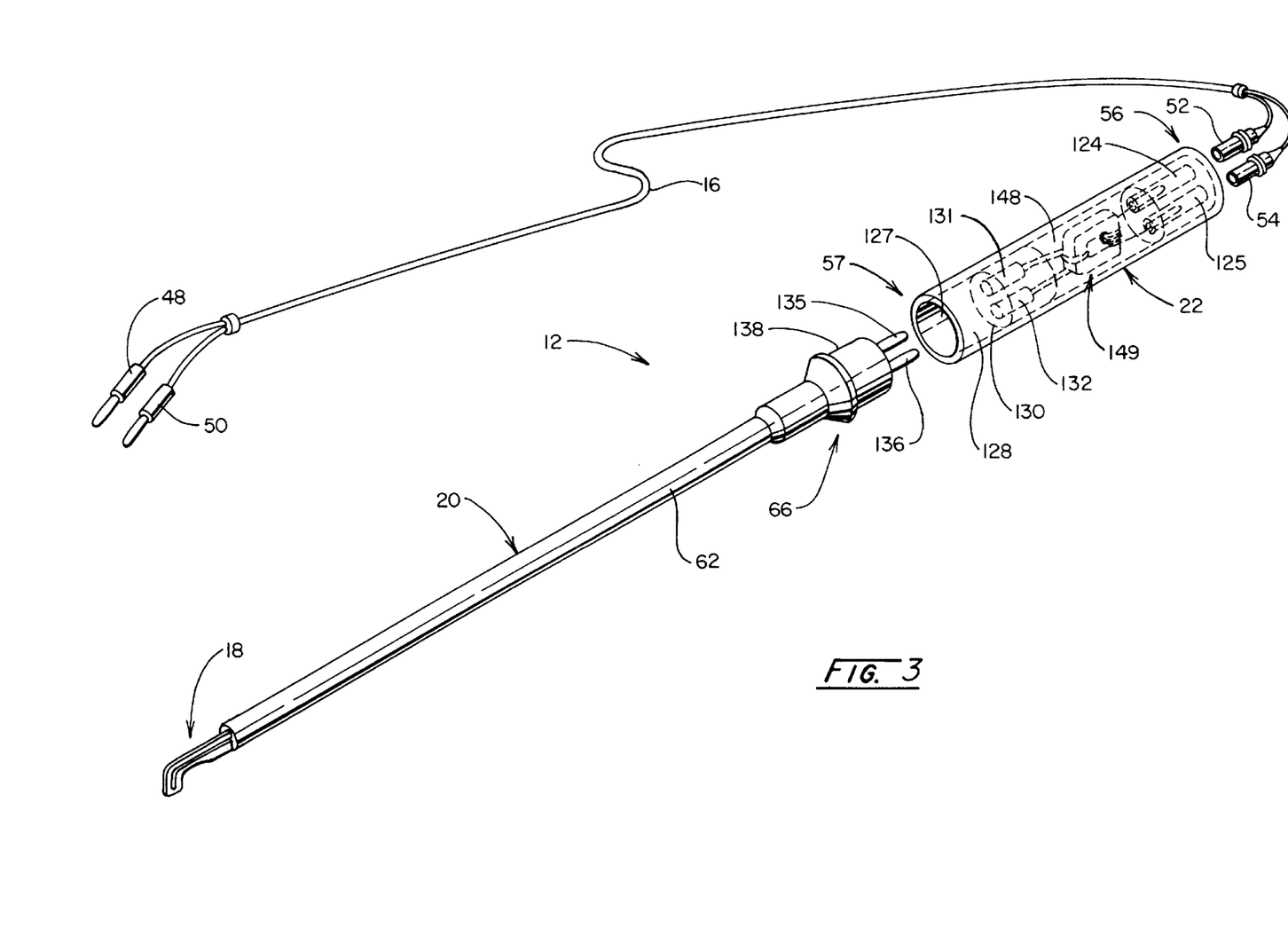
FIG. 3 is an exploded view of the surgical instrument of FIG. 1.

Turning to FIG. 3, shaft 20 is shown to be removably connectable with handle 22. Such removable connection between shaft 20 and handle 22 promotes a disposable design which permits economic re-use of handle 22. Additionally, such modular structuring permits changing to a new or different working end assembly. For example, a single surgical procedure may require several different working end configurations, such as a spatula shape, scalpel shape, hook shape, or other shape suitable for the surgical procedure being performed. A surgeon, thus, may quickly and easily remove one type of working end assembly and replace it with another. Additionally, re-usable handle 22 may be sterilized by commonly used sterilization techniques such as steam, dry heat, ethylene oxide, or liquid sterilizing agents. Handle 22 also incorporates a removable connection with cable 16 such that a variety of new or different handles or cables also may be employed.

Figure 4:
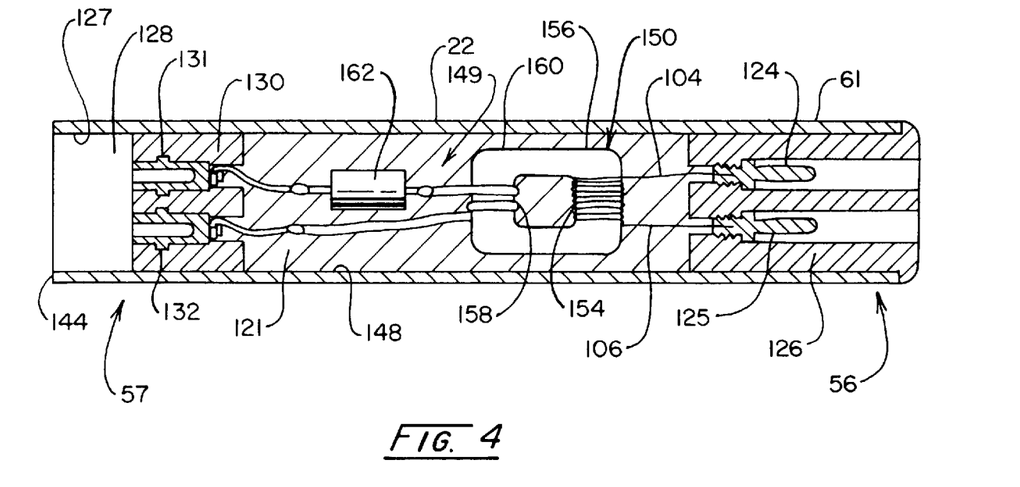
FIG. 4 is a partial sectional view of the handle component of the instrument of FIG. 1.

Looking to the connection between cable 16 and handle 22 in more detail and refering additionally to FIG. 4, instrument input 56 includes two male input connectors 124 and 125 located within handle 22. Input connectors 124 and 125 form part of a connector housing assembly 126 which is secured to the interior of casing 61 of handle 22 by, for example, an adhesive. Housing assembly 126 preferably is formed from an insulating polymeric material and input connectors 125 and 126 are formed from a suitable conductive material, such as copper. Cable output connectors 52 and 54 of cable 16, in turn, are shown as two female sockets. Each connector 124 and 125 is configured to removably receive a corresponding output connector 52 and 54. Additionally, cable input connectors 48 and 50 of cable 16 are provided as two male inserts which are removably connectable with output terminals 30 and 32 of generator 14 (FIG. 1).

Figure 5:
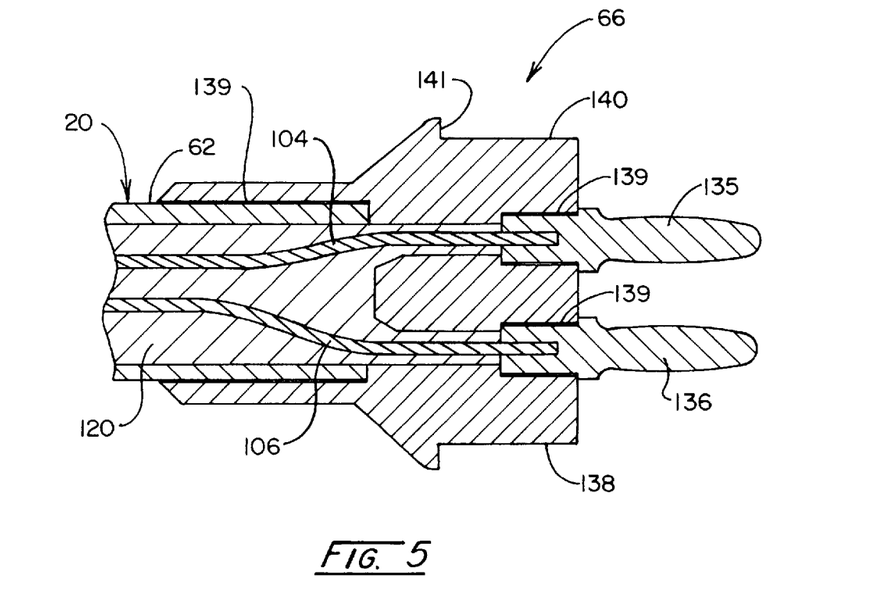
FIG. 5 is a partial cross sectional view of the surgical instrument of FIG. 1 taken along the plane 4—4 shown therein.

FIGS. 3, 4, and 5 reveal the features deriving removable connection between shaft 20 and handle 22. Instrument output 57 includes a cyclindrically configured receiving surface 127 which forms a cavity 128. An output connector housing assembly 130 is mounted within this cavity 128. Housing asembly 130 is formed from an insulating polymeric material and includes two female output connectors 131 and 132. Output connectors 131 and 132 are configured to removably receive corresponding male electrical input terminals 135 and 136. FIG. 5 shows that these input terminals 135 and 136 extend outwardly from a connector assembly 138 at end 66 of shaft 20. Connector assembly 138 is mounted over outer surface 62 and secured thereto by a suitable adhesive 139, such as an epoxy adhesive. A cyclindrically configured mount surface 140 forms one end of connector assembly 138. Assembly 138 is dimensioned to be received into cavity 128 to enable terminals 135 and 136 to be inserted within connectors 131 and 132. In this regard, when end 66 of shaft 20 is inserted into output 57, mount surface 140 is secured within cavity 128 and is adjacently abutted to the interior of receiving surface 127. An annular stop surface 141 is disposed at one end of mount surface 140 and provides an abutment against end 144 of receiving surface 127. Electrical communication between electrical input terminals 135 and 136 and legs 82 and 84 of support assembly 26 (FIG. 2) is provided by the earlier described leads 104 and 106. Connection, for example, may be by soldering, welding, or mechanical crimping. Additionally, electrical input terminals 135 and 136 are shown to extend into connector assembly 138 and may be secured therein with adhesive 139. Connector assembly 138 preferably is formed from an electrically insulating polymeric material. Additionally, an electrically insulating potting material 120, 121 is provided adjacent both connector assembly 138 and housing assembly 130, respectively.

An important feature of the present invention resides in the adaptation of surgical instrument 12 to use with conventional electrosurgical generators, i.e., the device does not require a complex control system or dedicated power source. Of particular note, surgical instrument 12 is able to effect impedance matching with conventional electrosurgicalgenerators. In this regard, turning to FIGS. 1, 3, and 4, it is revealed that handle 22 is provided with an inner cavity 148. Located within cavity 148 are circuit components 149 selected for effecting power transfer impedance matching between generator 14 and heating component 24. By properly selecting the resistance of heating component 24 and the impedance matching characteristics of circuit components 149, the output characteristics of generator 14 combine to advantageously perform with the intrinsic auto-regulating behavior of the ferromagnetic properties of heating component 24.

The impedance matching of a typical generator with heating component 24 can be accomplished using a transformer as at 150. Transformer 150 is constructed as having a ratio of first conductor lead turns 154 on primary side 156 to second conductor lead turns 158 on secondary side 160 of about 5:1 to 10:1. This ratio will depend on the impedance characteristics of heating component 24 over its operating temperature range and the change in output of generator 14 in accordance with load impedances. The core material for transformer 150 is selected to provide efficient coupling between the electromagnetic fields of the primary and secondary windings at the operating frequency of generator 14, which for a typical commercially available generator ranges from about 350 KHz to 1 MHz. A preferred core material is magnesium zinc ferrite which is manufactured by Magnetics Division of Sprang & Co., Butler, Pa.

The power supplied by generator 14 to heating component 24 may be increased through the use of various circuit tuning techniques. By way of example, a capacitor 162 may be placed in series on secondary side 160 of transformer 150. The capacitance value of capacitor 162 is selected based on the reactance of circuit components 149 which, in turn, is dependent on the frequency of generator 14. Accordingly, a specific capacitance for capacitor 162 is selected to optimize power delivery corresponding to the output frequency of generator 14. For example, the capacitance value of capacitor 162 may be selected for use with generators operating in the 400 KHz range or decreased for use with generators operating in the 500 to 600 KHz range. For those generators operating at even higher frequencies, the capacitance value for capacitor 162 may be further decreased. In each case, the value selected should be based on maximum power delivery to heating component 24 under cutting and coagulating conditions. Cavity 148 preferably is filled with a potting material 121, for example, similar to that shown at 120 and suitable for encapsulation of transformer components.

As an additional feature, these conventional electrosurgical generators may be used in conjunction with the invention to enhance the auto-regulative behavior of ferromagnetic heating component 24. Auto-regulation is achieved through the use of a bipolar output voltage change with load impedance as is graphically illustrated at 168 in FIG. 6. Looking to that figure, graph 168 is plotted as having a horizontal or X-axis represented by ohmic load impedance and a vertical or Y-axis represented by bipolar output voltage. Curve 170 of the graph is representative of values typical for commercially available electrosurgical generators having bipolar outputs. As illustrated, the output voltage of generator 14 decreases with decreasing load impedance, and, in particular, decreases sharply as the load impedance decreases below about 20 to 50 ohms. The invention employs this output voltage characteristic to improve the auto-regulating behavior of heating component 24. In this regard, as the skin depth through which high frequency RF current flows increases, a concomitant decrease occurs in both the resistance of the ferromagnetic heating component 24 and, as illustrated by curve 170, the output voltage of generator 14. This decrease in the applied voltage in regions where the slope of curve 170 is greater than unity causes the current flowing in heating component 24 to decrease according to Ohm's law (current is equal to applied voltage divided by resistance). As the current flowing through heating component 24 decreases, the heating rate decreases according to the product of the square of the current and the resistance.

Figure 7:
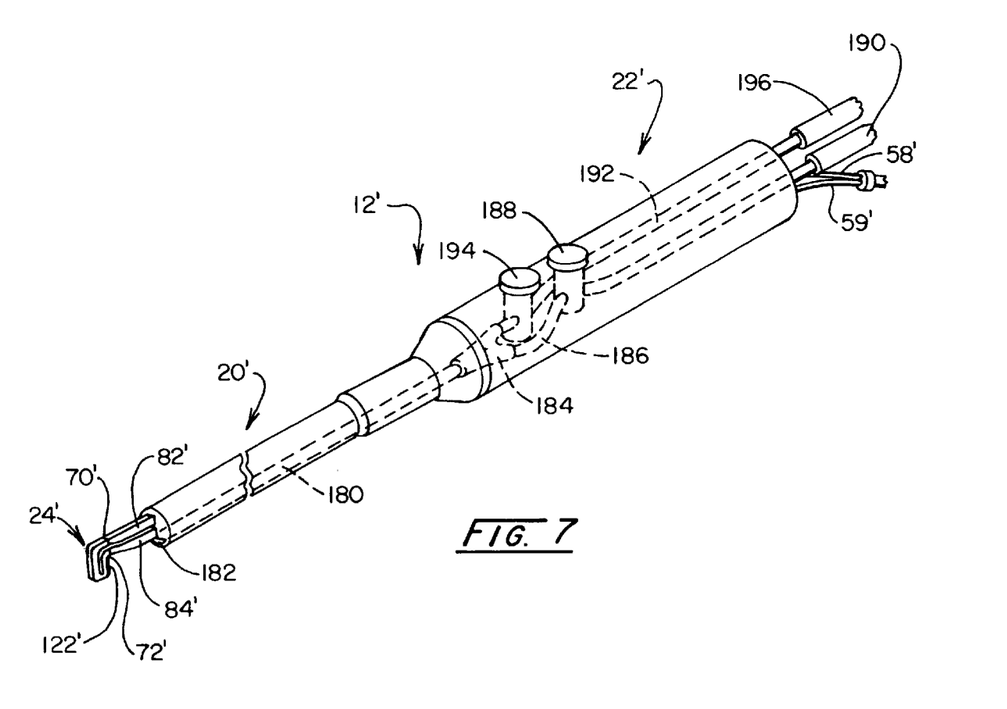
FIG. 7 is a partial perspective view of an instrument as shown in FIG. 1 with irrigating and aspirating features.

Referring to FIG. 7, an adaptation which may be found to be beneficial to the instrument 12 is shown in schematic perspective. In the figure, where appropriate, the same numeration is utilized to identify the same components earlier-described in connection with instrument 12 but in primed fashion. For the instrument 12' approach, an arrangement is incorporated wherein the instrument may supply irrigant such as isotonic saline solution to the instrument working end. In the present embodiment, a singular conduit shown in phantom at 180 is seen to extend along shaft 20' to an opening 182 located in proximity to the junction of legs 82' and 84' with shaft 20'. Thus, irrigant fluid may be expressed somewhat directly toward the cutting portion 122' of the heating component 24'. This same conduit 180 may be employed to aspirate the expressed irrigant fluid or, as is apparent, dedicated conduits may be employed. For the embodiment shown, however, conduit 180 is seen to extend into the handle portion 22' whereupon it is coupled to a Y fitting 184. One leg of the Y fitting 184 is connected to a conduit dedicated to expressing irrigant fluid as seen at 186. A thumb actuated pinch valve 188 controls the flow of fluid in conduit 186, which conduit is seen to extend outwardly from handle 22' for connection with a feeder line provided as a flexible tube 190. Aspiration is achieved by applying subatmospheric pressure to conduit 192 which extends to the opposite leg of Y connector 184 through a pinch valve 194. Connection to the source of subatmospheric or back pressure or vacuum is through a flexible conduit 196 connected to conduit 192 at the rear of handle 22'.

The combination of an irrigant and aspiration feature with the resistive heating approach of the invention resides in the fact that conducting fluids safely can be used as irrigants without the risk of exposing the handle or fluid lines to the high voltage level otherwise present, for example, with monopolar electrosurgical instruments.

In another embodiment of the present invention, heating component 24, shown in FIG. 1, may be constructed using a material having a large negative temperature coefficient (NTC) of resistance instead of ferromagnetic material. Such materials include, for example, silicon carbide and alloys of silicon and germanium and preferably having an electrical resistivity from about 1000 micro-ohm-centimeters to about 10 ohm-centimeters. A heating component formed from NTC material exhibits the noted attributes of auto-regulation which may be combined with the above-described impedance matching features.

A conventional electrosurgical generator may be used with a heating component formed of large NTC resistive material to achieve the noted auto-regulative behavior. Turning to FIGS. 1 and 4, circuit components 149 may be selected in accordance with the impedance matching characteristics exhibited between heating component 24 and conventional generator 14. In this regard, the ratio of first conductor lead turns 154 on primary side 156 of transformer 150 to second conductor lead turns 158 on secondary side 160 can be optimized according to the impedance of the resistive load associated with the NTC material. Additionally, the capacitance value of capacitor 162 may be selected based on the frequency of generator 14. A specific capacitance for capacitor 162 then can be selected to optimize power delivery corresponding to the output frequency of conventional generator 14.

Figure 6:
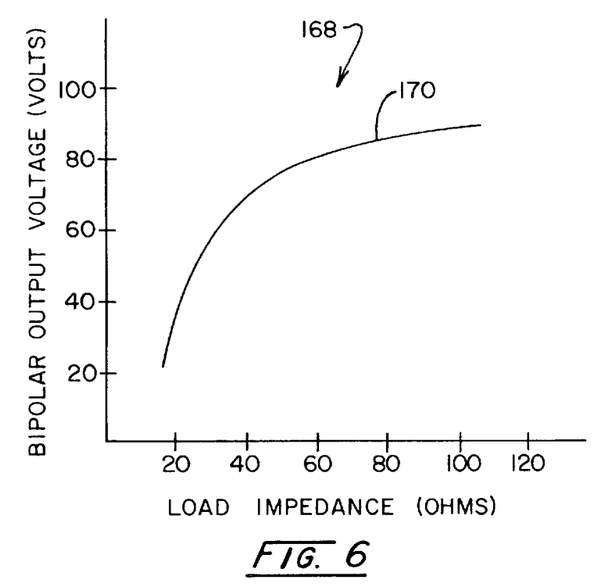
FIG. 6 is a graph depicting load impedance versus bipolar output voltage for a conventional electrosurgical generator.

Conventional electrosurgical generators also may be employed in conjunction with the invention to enhance the auto-regulative behavior of heating component 24 formed of NTC resistive material. In this embodiment, the temperature of heating component 24 tends to increase when tissue engaging region 74 is in contact with tissue, i.e., exposed to a greater cooling load. However, once heating component 24 is brought out of contact with tissue an into contact with air, i.e., exposed to a lesser cooling load, the temperature of tissue engaging region 74 decreases. Turning also to FIG. 6, it is revealed that since the bipolar voltage output of conventional electrosurgical generator 14 decrease rapidly with decreasing load resistance at resistance values below 20 to 50 ohms, the decreasing resistance of heating component 24 causes the power delivered thereto to decrease. In turn, this decrease in power delivery reduces the level of resistance heating. Thus, the intrinsic behavior of heating component 24 formed using a NTC material combined with the use of the output voltage characteristics of conventional electrosurgical generators provides for self-regulation of temperature.

In yet another embodiment, the material for heating component 24 may be selected from metals or alloys having a small temperature coefficient of resistance, such as Nichrome V containing 80% nickel and 20% chromium. In this embodiment, heating component 24 is coated with a high radiation emittance coating or otherwise preoxidized to maximize emittance.

Looking next to FIGS. 8–11, wherein like parts are designated with like numerals but with differing alphabetical suffixes, several alternative embodiments to working end assembly 18 described in FIG. 2 are shown. Each of these figures shows a respective working end assembly 18A–18D, a partial view of shaft 20A–20D and outer surface 62A–62D. Each shaft as identified at 20A–20D also includes a corresponding cap assembly shown respectively at 94A–94D which is similar to cap assembly 94. Save for the geometric configurations and other noted differences, working end assemblies 18A–18A and shafts 20A–20D substantially are similar to the working end assembly 18 and shaft 20 described hereinbefore.

Figure 8:
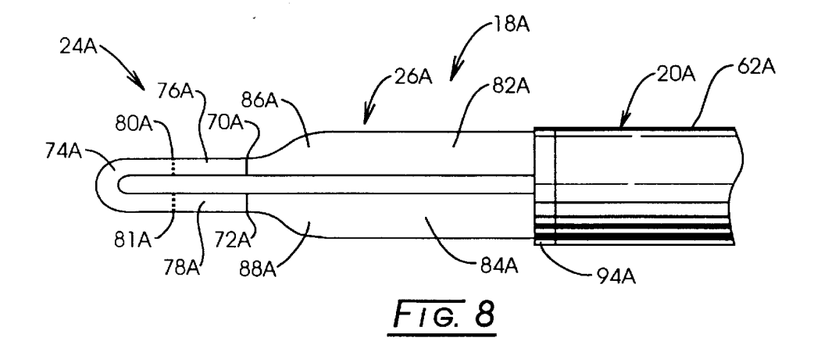
FIG. 8 is a plan view of a working end assembly which may be employed with the surgical instrument of FIG. 1.

Looking then to FIG. 8, a probe-shaped heating component 24A is shown. Working end assembly 18A includes a support assembly 26A configured as having two legs 82A and 84A extending from shaft 20A to leg ends 86A and 88A. Heating component 24A extends continuously from a first terminus 70A to define a tissue engaging region 74A, and thence to a second terminus 72A. Two thermal transition regions 76A and 78A, respectively, are located at predetermined inward extents from first and second termini 70A and 72A to borders 80A and 81A. These transition regions 76A and 78A extend a distance effective to restrict the temperature levels exhibited at support assembly 26A to values atraumatic to tissue and organs while the tissue engaging region 74A is elevated to temperatures effective to provide hemostasis. No cutting edge is provided within tissue engaging region 74A since heating component 24A is employed predominantly for hemostasis and not for cutting.

Figure 9:
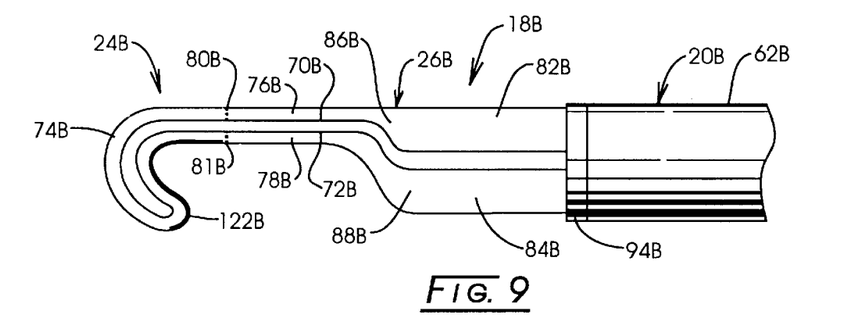
FIG. 9 is a plan view of another working end assembly which may be employed with the surgical instrument of FIG. 1.

Turning next to FIG. 9, a hook-shaped heating component 24B is shown. Working end assembly 18B includes a support assembly 26B configured as having two legs 82B and 84B which extend from shaft 20B to leg ends 86B and 88B. Heating component 24B extends continuously from a first terminus 70B to define a tissue engaging region 74B, and then to a second terminus 72B. Two thermal transition regions 76B and 78B, respectively, are located predetermined inward extents from first and second termini 70B and 72B to borders 80B and 81B. These transition regions 76B and 78B again extend a distance effective to restrict the temperature levels exhibited at support assembly 26B to values atraumatic to tissue and organs while the tissue engaging region 74B is elevated to temperatures effective to cut tissue and provide simultaneous hemostasis. A cutting edge 122B may be provided along the inside edge of the hook.

Figure 10:
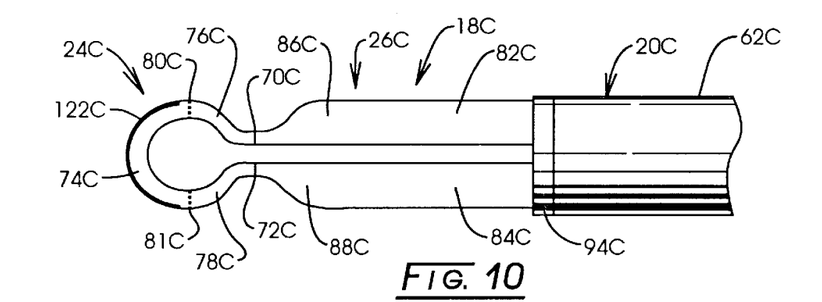
FIG. 10 is a plan view of still another working end assembly which may be employed with the surgical instrument of FIG. 1.

FIG. 10 reveals a spatula shaped heating component 24C. In this embodiment, support assembly 26C includes two legs 82C and 84C extending from shaft 20C to leg ends 86C and 88C. Heating component 24C has a first terminus 70C which extends continuously to define a tissue engaging region 74C, and thence to a second terminus 72C. Two thermal transition regions 76C and 78C, respectively, are located at predetermined inward extents from first and second termini 70C and 72C to respective borders 80C and 81C. These transition regions 76C and 78C extend a distance effective to restrict the temperature levels exhibited at support assembly 26C to values atraumatic to tissue and organs while the tissue engaging region 74C is elevated to temperatures effective to cut tissue and provide simultaneous hemostasis. A cutting edge 122C is located along the outer periphery of tissue engaging region 74C.

Figure 11:
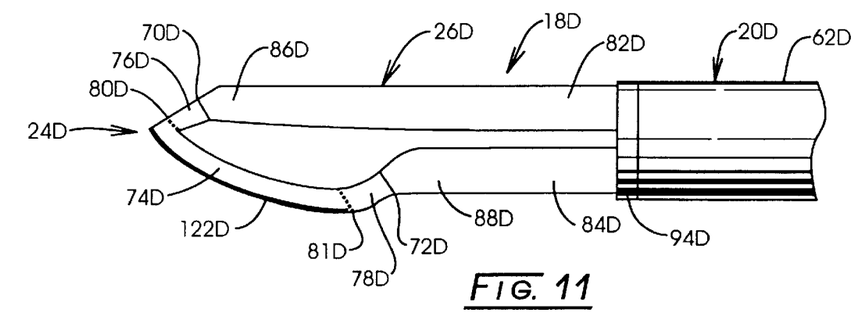
FIG. 11 is a plan view of another working end assembly which may be employed with the surgical instrument of FIG. 1.

Lastly, FIG. 11 depicts a scalpel shaped heating component 24D provided with a tissue engaging region 74D located along the outer perimeter of a scimitar-shaped scalpel. This embodiment includes a support assembly 26D having two legs 82D and 84D which extend from shaft 20D to leg ends 86D and 88D. Heating component 24D extends continuously from a first terminus 70D to define a tissue engaging region 74D, and thence to a second terminus 72D. Two thermal transition regions 76D and 78D, respectively, are located at predetermined inward extents from first and second termini 70D and 72D to borders 80D and 81D. These transition regions 76D and 78D extend a distance effective to restrict the temperature levels exhibited at support assembly 26D to values atraumatic to tissue and organs while the tissue engaging region 74D is elevated to temperatures effective to cut tissue and provide simultaneous hemostasis. A cutting edge 122D is provided along the periphery of tissue engaging region 24D.

Since certain changes may be made in the above-described apparatus and system without departing from the scope of the invention herein involved, it is intended that all matter contained in the description thereof or shown in the accompanying drawings shall be interpreted as illustrative and not in a limiting sense.

What is claimed:

1. A system for carrying out the thermal and hemostatic cutting of tissue, comprising:

an electrosurgical generator having bipolar output terminals exhibiting a load impedance to voltage characteristic, said generator exhibiting an operating frequency range characteristic at said output terminals within a range from about 350 KHz to 1 MHz;

a surgical instrument including an electrical resistance heating component having a region responsive to an applied variable voltage and current to attain a temperature below Curie temperature effective to cut said tissue upon entering contact therewith and exhibiting a predetermined load impedance to said current;

a support assembly coupled at a first end with said heating component for effecting its support and applying said current thereto, and having a shaft portion with electrical input terminals disposed at a second end;

a hand engageable instrument handling portion having circuit components selected for effecting power transfer impedance matching within said range of frequencies between said bipolar output terminals and said heating component, said circuit components including a transformer having a primary to secondary turns ratio selected within a range of about 5:1 to about 10:1 and including a capacitor coupled with said transformer having a capacitance value selected with respect to said operating frequency range for optimizing power transfer to said heating component, said instrument handling portion having an instrument output coupled with said support assembly electrical input terminals, and having an instrument input; and an elongate cable connectable in electrical power transfer relationship between said bipolar output terminals of said electrosurgical generator and said instrument input of said instrument handling portion.

2. The system of claim 1 in which:

said electrical resistance heating component is formed of thermally autoregulating material; and said electrosurgical generator given load impedance to voltage characteristic promotes the thermal autoregulation of said electrical resistance heating component.

3. The system of claim 1 in which:

said instrument output of said instrument handling portion includes two electrical output connectors which are removably connectable in electrical communication with said electrical input terminals of said support assembly;

said instrument input of said instrument handling portion includes two electrical input connectors; and said cable includes two connectors removably connectable in electrical communication with said two electrical input connectors.

* * * * *